United States Patent [19]
Hibino et al.

[11] Patent Number: 5,693,629
[45] Date of Patent: Dec. 2, 1997

[54] PROGESTERONE COMPOUND AND USE THEREOF

[75] Inventors: Satoshi Hibino; Eiichi Sugino, both of Fukuyama; Tetsuya Kohno, Machida; Shiho Fujimori, Odawara; Hideo Nemoto, Miyagi; Yoshitatsu Ichihara; Yoshio Sato, both of Odawara, all of Japan

[73] Assignee: Meiji Milk Products Co., Ltd., Tokyo, Japan

[21] Appl. No.: 716,325

[22] PCT Filed: Apr. 3, 1995

[86] PCT No.: PCT/JP95/00642

§ 371 Date: Oct. 4, 1996

§ 102(e) Date: Oct. 4, 1996

[87] PCT Pub. No.: WO95/26974

PCT Pub. Date: Oct. 12, 1995

[30] Foreign Application Priority Data

Apr. 4, 1994 [JP] Japan ................. 6-066246

[51] Int. Cl.[6] ................. A61K 31/56; C07J 3/00
[52] U.S. Cl. ................. 514/180; 552/610
[58] Field of Search ................. 514/180; 552/610

[56] References Cited

U.S. PATENT DOCUMENTS

| | | | |
|---|---|---|---|
| 4,198,403 | 4/1980 | Alvarez | 424/241 |
| 4,261,984 | 4/1981 | Alvarez | 424/238 |
| 4,710,495 | 12/1987 | Bodor | 31/58 |
| 4,946,834 | 8/1990 | Holt et al. | 514/119 |
| 4,996,335 | 2/1991 | Bodor | 552/610 |

OTHER PUBLICATIONS

Chemical Abstracts, vol. 120, No. 21, May 23, 1994, AN-261586a, T. Yamamoto, et al., "Angiostatic Activities of Medroxyprogesterone Acetate and Its Analogs".

Chemical Abstracts, vol. 119, No. 7, Aug. 16, 1993, AN-063464a, F. Blei, et al., "Mechanism of Action of Angiostatic Steroids: Suppression of Plasminogen Activator Activity Via Stimulation of Plasminogen Activator Inhibitor Synthesis".

Chemical Abstracts, vol. 117, No. 11, Sep. 14, 1992, AN-104554j, H. Jikihara, et al., "Inhibitory Effect of Medroxyprogesterone Acetate on Angiogenesis Induced by Human Endometrial Cancer".

Journal of Organic Chemistry, vol. 28, No. 10, pp. 2633-2640, Oct. 1963, C. Bergstrom, et al., "9Alpha.-Fluoro-11-Deoxy Steroids".

*Primary Examiner*—Kimberly J. Prior
*Attorney, Agent, or Firm*—Oblon, Spivak, McClelland, Maier & Neustadt, P.C.

[57] ABSTRACT

A progesterone compound represented by the following formula (1):

[wherein $R^1$ represents a C1–C23 hydrocarbon group], and a neovascularization inhibitor containing the same as the active ingredient.

The compound (1) has a potent neovascularization inhibitory effect and is hence useful in the treatment of malignant tumors, diabetic retinitis, rheumatism, etc.

6 Claims, No Drawings

PROGESTERONE COMPOUND AND USE THEREOF

This application is a 371 of PCT/JP95/00642 filed Apr. 3, 1995.

TECHNICAL FIELD

The present invention relates to asteroid compound, and more particularly to a novel progesterone compound which has excellent neovascularization inhibitory action, and thus is useful as a remedy for malignant tumors, diabetic retinitis, rheumatism, etc. The invention also relates to neovascularization inhibitors containing the compound as the active ingredient.

BACKGROUND ART

Malignant tumors, diabetic retinitis, rheumatism, etc. are known as diseases in which neovascularization participates critically in the cause of disease or aggravation of pathology. Among such diseases, malignant tumors have widely been studied with respect to their relation to neovascularization, and it has come to be elucidated that neovascularization is crucial in the metastasis and prognosis of malignant tumors.

Recently, some substances exhibiting neovascularization activity have been reported. As such substances, there are known, for example, sulfated polysaccharides, platelet factor-4 (PF-4), pentosan polysulfates, TNP-470 (an analog of a mold product) tissue metalloproteinase inhibitors (TIMP), and minocycline. However, neovascularization inhibitory actions of these substances are not necessarily satisfactory, and there remains a need for development of neovascularization inhibitors with more excellent effects.

Estrogen is closely related to the genesis of endometrial carcinoma and mammary carcinoma, and therefore, antiestrogen agents and high doses of progestogen have been used for their treatment. Specifically, medroxyprogesterone acetate, a progestogen, has been used as a remedy for mammary carcinoma and endometrial carcinoma. It has recently been reported that medroxyprogesterone acetate has neovascularization inhibitory action.

However, when the present inventors examined the neovascularization inhibitory action of medroxyprogesterone acetate, they found its action to be weak, and thus it is questionable was to whether medroxyprogesterone acetate manifests its effect at an ordinary clinical dose.

Accordingly, an object of the present invention is to provide a novel progesterone derivative having excellent neovascularization inhibitory action.

DISCLOSURE OF THE INVENTION

The present inventors synthesized a huge number of progesterone derivatives and screened them not only for their progestogen action but also for their neovascularization inhibitory action. As a result, they found that the 9α-fluoro-6α-methylprogesterone derivative represented by the following formula (1) exhibits neovascularization inhibitory activity not less than 20 times as potent as that of medroxyprogesterone acetate. The present invention was accomplished based on this finding.

Accordingly, the present invention provides a progesterone compound represented by the following formula (1):

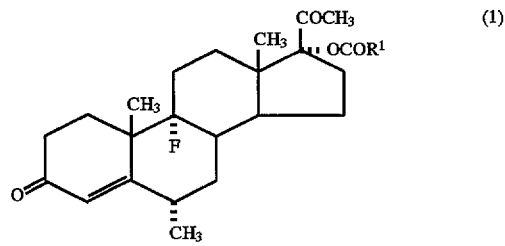

[wherein $R^1$ represents a C1–C23 hydrocarbon group].

The present invention also provides a neovascularization inhibitory agent containing the progesterone compound of formula (1) as an active component.

The present invention also provides a pharmaceutical composition containing the progesterone compound of formula (1) and a carrier for pharmaceuticals.

The present invention also provides use of the progesterone compound of formula (1) as a pharmaceutical.

The present invention also provides a method for the treatment of malignant tumors, diabetic retinopathy, and rheumatism, characterized by administering an effective amount of the progesterone compound of formula (1).

BEST MODE FOR CARRYING OUT THE INVENTION

In formula (1), which represents the progesterone compound of the present invention, examples of the hydrocarbon group $R^1$ include C1–C23 linear or branched or cyclic alkyl or alkenyl groups, with C1–C17 alkyl groups being more preferred. Specific examples of particularly preferred $R^1$ groups include methyl, ethyl, n-propyl, isopropyl, n-butyl, n-pentyl, n-hexyl, n-heptyl, n-octyl, n-nonyl, n-decyl, n-dodecyl, n-tridecyl, n-tetradecyl, and n-pentadecyl. Of these, methyl and n-pentadecyl are particularly preferred.

The progesterone compound of formula (1) of the present invention may be prepared in accordance with either of the following reaction schemes A or B.

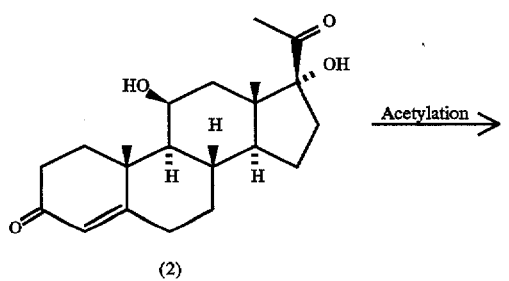

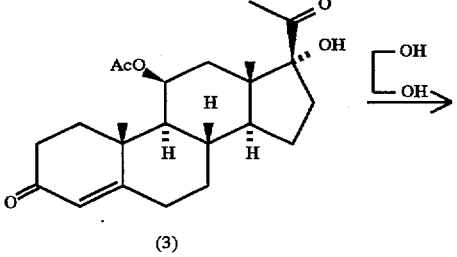

-continued
<Reaction scheme A>

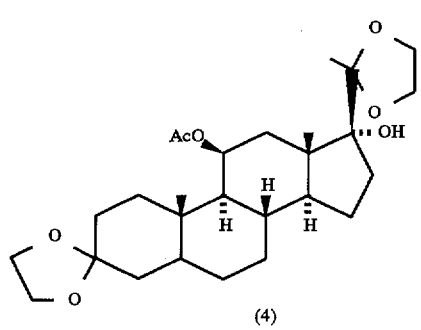
(4)

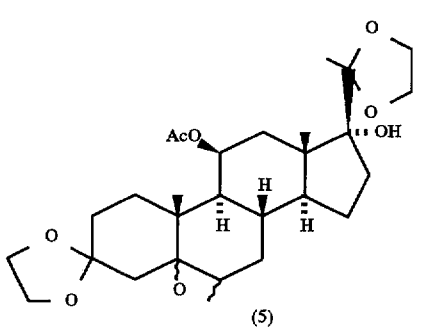
(5)

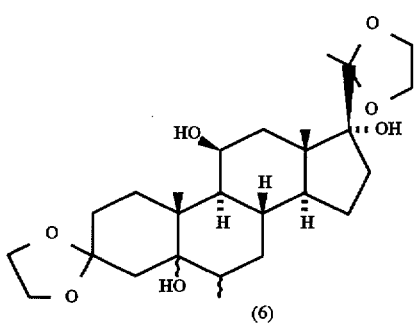
(6)

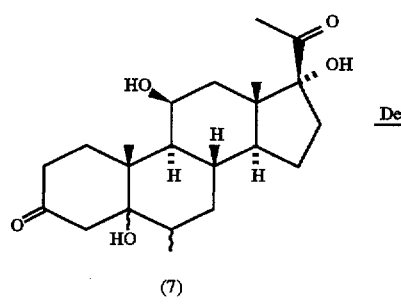
(7)

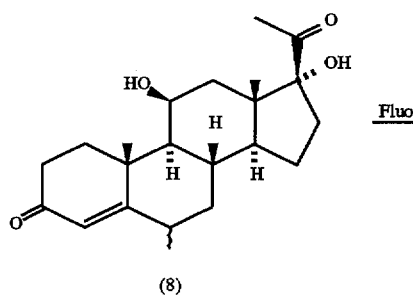
(8)

-continued
<Reaction scheme A>

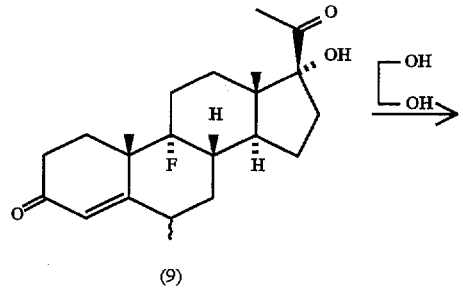
(9)

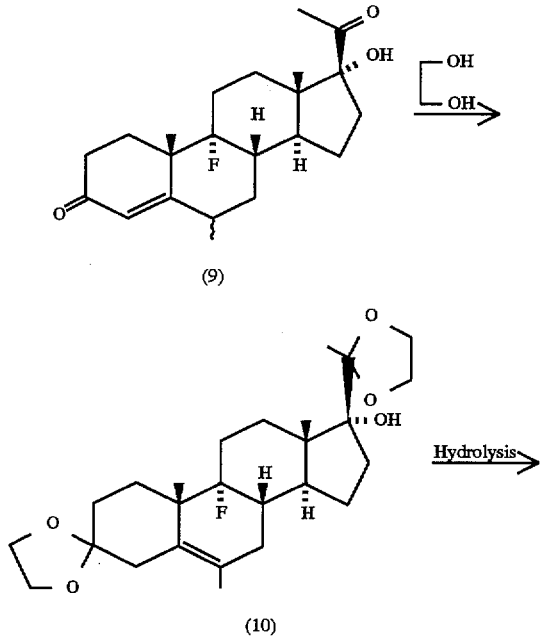
(10)

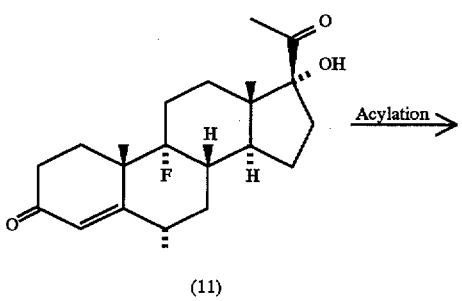
(11)

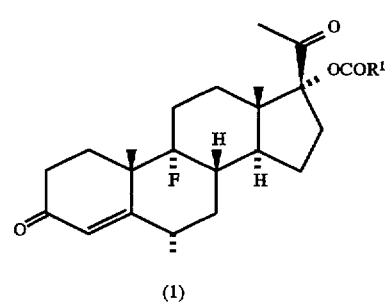
(1)

[wherein $R^1$ has the same meaning as defined above].

Briefly, a pregnenediol (2) is acetylated to obtain a 11β-acetoxy derivative (3). Ethylene glycol is reacted therewith to protect the ketone, and is subjected to oxidation and then methylation so as to introduce a methyl group at the 6-position. When the resultant 6-methyl derivative (6) is hydrolyzed, dehydrated, and then fluorinated, a 9α-fluorinated derivative (9) is obtained. Ketalization of 9α-fluorinated derivative (9) and hydrolysis of ketal group gave a 9α-fluoro-6α-methyl derivative (11), which is subsequently acylated to obtain a compound (1) of the present invention.

The acetylation reaction of pregnanediol (2) is carried out by reacting an acetylating agent typified by acetic anhydride with pregnanediol (2) in the presence of a base such as 4-dimethylaminopyridine. Also, ketalization of the resultant 11β-acetoxy derivative (3) is carried out by reacting ethylene glycol with the derivative (3) in the presence of a condensing agent such as p-toluene sulfonic acid. Oxidation of compound (4), which is performed using a peracid typified by m-chloroperbenzoic acid, produces a 5,6-epoxy derivative (5). Methylation of the 5,6-epoxy derivative (5) is preferably performed using a Grignard reagent such as magnesium methyl bromide. Hydrolysis of the resultant 6-methylated product (6) is preferably performed using a weak base such as potassium hydrogen sulfate, sodium hydrogen carbonate, and sodium carbonate. The resultant compound (7) is dehydrated with sodium hydroxide, potassium hydroxide, etc. Compound (8) is fluorinated by reacting hydrogen fluoride-pyridine with compound (8). 6-Methyl-9α-fluoro derivative (9) may be ketaled in a manner similar to that mentioned above using ethylene glycol, and the resultant ketal (10) may be hydrolized using a weak acid as described above. Acylation of the resultant 9α-fluoro-6α-methyl derivative (11) is preferably performed by reacting the derivative (11) with a reactive derivative of carboxylic acid (R¹COOH) such as acid anhydride, acid halide, etc. in the presence of a condensing agent such as p-toluenesulfonic acid.

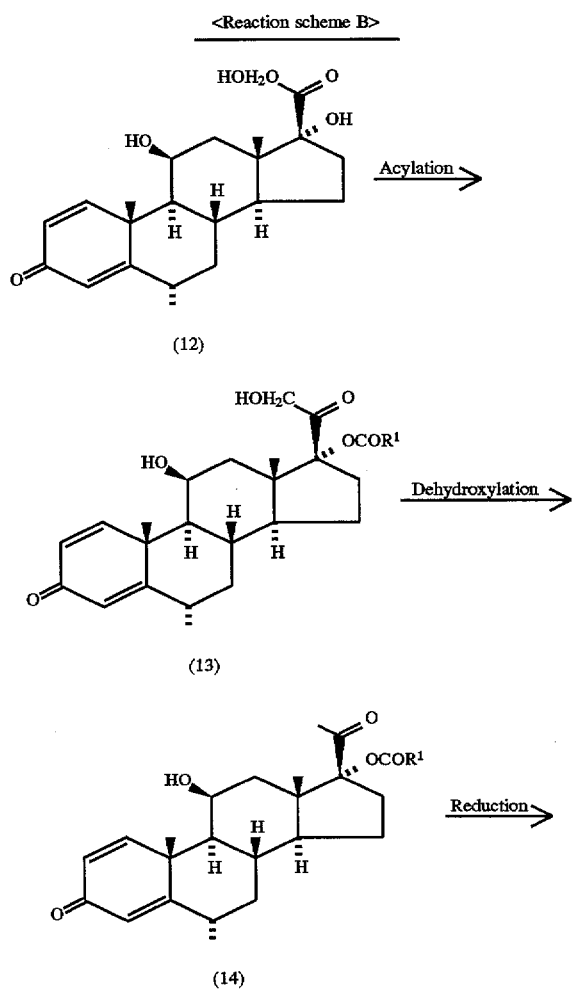

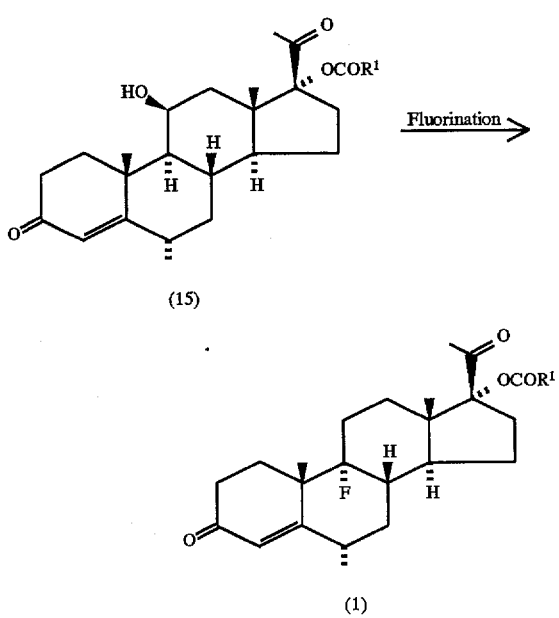

[wherein R¹ has the same meaning as defined above].

Briefly, the hydroxy group at the 17- position of 6α-methylpredonisolone (12) is acylated to obtain a 17α-acylated product (13), which is then dehydroxylated to obtain a methylated product (14). When the double bond at the 1-position of the product (14) is reduced, an enone derivative (15) is obtained. Subsequent introduction of a fluorine atom into the 9α- position of the enone derivative affords the compound (1) of the present invention.

Acylation of the 6α-methylpredonisolone (12) is performed through a two step reaction; reacting the compound (12) with trimethyl ortho- acetate or a similar material, and then hydrolyzing the ortho- ester. The hydroxyl group of the resultant 17α-acylated product (13) is removed by first reacting the product (13) with methanesulfonyl chloride and then refluxing with heat in the presence of methyl iodide. The obtained methylated product (14) is reduced via hydrogenation in the presence of a metal catalyst such as chlorotris (triphenylphosphine)rhodium (I), etc. Fluorination of the enone derivative is performed by the reaction with hydrogen fluoride in the presence of pyridine, etc.

The thus-obtained compound (1) of the present invention exhibits excellent neovascularization inhibiting action with hormonal activities being eliminated. Therefore, the compound (1) can be used in the treatment of malignant tumors, diabetic retinitis, rheumatism, etc. as a neovascularization inhibitor.

When the compound (1) of the present invention is used for the above-mentioned purposes, it is preferably used after being prepared into a pharmaceutical composition together with an ordinarily used pharmaceutical carrier. Such pharmaceutical compositions may be oral preparations such as tablets, granules, and capsules; injections; per rectum preparations; and transdermal preparations. When these compositions are prepared, carriers for pharmaceuticals may be employed, including vehicles, binders, disintegrants, solubilizers, and flavoring agents.

When the compound (1) of the present invention is used as a neovascularization inhibitor, the dose is preferably from 0.1 to 600 mg per day for an adult/kg/day which is divided in 1 to 5 times, though it may differ according to the administration route, patient's condition, age, body weight, etc.

EXAMPLES

The present invention will next be described in detail by way of examples, which should not be construed as limiting the invention.

Example 1

(1) 11β-Acetoxy-17α-hydroxy-4-pregnene-3,20-dione (3)

A mixture of 4-pregnene-11β,17α-diol-3,20-dione (2) (2 g), acetic anhydride (10 ml), pyridine (20 ml) and 4-dimethylaminopyridine (20 mg) was stirred for 6 hours at room temperature. The reaction mixture was diluted with water (50 ml) and extracted with chloroform. The chloroform layer was sequentially washed with 10% HCl, a 5% aqueous $NaHCO_3$ solution, and brine, dried over $Na_2SO_4$, and concentrated. The residue was subjected to column chromatography (silica gel, 150 g) using 70% chloroform/hexane as eluant, thereby obtaining an acetylated derivative (3) (2.24 g, 100%). Recrystallization from ethyl acetate/hexane afforded white crystals having a melting point of 159.5°–160° C.

$^1$H-NMR ($CDCl_3$): δ 0.85(3H, s), 2.01 (3H, s), 2.21(3H, s), 3.04(2H, m), 5.34–5.56(1H, m), 5.65(1H, s).

MS:m/z388 ($M^+$).

Elementary analysis for $C_{23}H_{32}O_5$: Calculated: C 71.10; H 8.30 Found: C 71.08; H 8.50

(2) 6-Methyl-4-pregnene-11β,17α-diol-3,20-dione (8)

11-Acetate (3) (2 g), ethylene glycol (1.1 g), and p-toluenesulfonic acid.1H2O (40 mg) were refluxed in benzene (100 ml) for 7 hours while preventing humidity (by the use of a reflux condenser equipped with a moisture separator). After the temperature of the reaction mixture was returned to room temperature, the mixture was washed with brine, dried over $Na_2SO_4$, and concentrated. (The residue is used directly in the next step.) 70% m-chloroperbenzoic acid (2 g) was added to the residue (4) (2 g) in chloroform (150 ml), and the mixture was stirred for 12 hours at room temperature. The reaction was sequentially washed with an aqueous $Na_2CO_3$ solution and brine, and then concentrated. The resultant residue (5) is thoroughly dried, and then dissolved in anhydrous tetrahydrofuran (30 ml). While vigorously stirring the mixture, magnesium methyl bromide (30 ml, 1.02M tetrahydrofuran solution) was added. The reaction mixture was refluxed for 18 hours, the temperature returned to room temperature, and the contents poured in iced water containing ammonium chloride. The mixture was extracted with chloroform, and the chloroform layer was washed with saturated brine, dried over $Na_2SO_4$, and concentrated. The residue (6) was refluxed at 70° C. for 2 hours in a mixture of acetone (80 ml) and an aqueous 5% $KHSO_4$ solution (40 ml). The solvent was evaporated, and the residue was extracted with chloroform. The chloroform layer was washed with saturated brine, dried over $Na_2SO_4$, and concentrated. Subsequently, the residue (7) was stirred for 2 hours in a mixture of 0.05N NaOH (100 ml) and methanol (100 ml) at room temperature. Acetic acid (1 ml) was added to the reaction mixture, and the mixture was concentrated to ca. a half volume. Extraction was performed using chloroform. The chloroform layer was washed with brine, dried over $Na_2SO_4$, and concentrated. The residue was subjected to column chromatography (silica gel, 70 g) using 30% ethyl acetate/hexane as eluant, thereby obtaining the title compound (8) (23%, from compound (3)). Recrystallization from ethyl acetate afforded white crystals having a melting point of 221°–225° C.

[α] +64.6° (MeOH).

$^1$H-NMR ($CDCl_3$): δ 1.03(3H, s), 1.05(3H, s), 1.06(3H, d, J=7.33Hz), 1.27(3H, d, J=7.57Hz), 1.42(3H, s), 1.50(3H, s), 2.29(3H, s), 2.30(3H, s), 2.68–2.71(2H, m), 3.48(1H, q, J=7.01Hz), 4.47(1H, d, J=2.43Hz), 5.73(1H, s).

MS:m/z360($M^+$).

Elementary analysis for $C_{22}H_{32}O_4$: Calculated: C 73.30; H 8.95 Found: C 73.40; H 8.99

(3) 9α-Fluoro-17α-hydroxy-6-methyl-4-pregnene-3,20-dione (9)

Hydrogen fluoride-pyridine [4 ml, HF:pyridine=7:3 (w/w)] were placed in a Teflon container. While maintaining the exterior temperature at −15° C. under nitrogen, 11β-hydroxy-6-methyl-4-pregnane-3,20-dione (9) (200 mg) was added. The mixture was stirred for 60 hours at the same temperature, and subsequently, the mixture was sequentially washed with 3% HCl, 5% $NaHCO_3$, and brine, dried over $Na_2SO_4$, and concentrated. The residue was subjected to column chromatography (silica gel, 30 g) using 30% ethyl acetate/hexane as eluant, thereby obtaining a fluorinated compound (9) (47 mg, 23.3%). Recrystallization from ethyl acetate afforded white crystals having a melting point of 232°–235° C.

$^1$H-NMR ($CDCl_3$): δ 0.75(3H, s), 0.78(3H, s), 1.11(3H, d, J=6.35Hz), 1.20(3H, d, J=4.96Hz), 1.30(3H, s), 1.37(3H, s), 2.27(3H, s), 2.28(3H, s), 2.69–2.75(2H, m), 2.99–3.07(1H, m), 3.82(1H, d, J=1.84Hz), 5.85(1H, d, J=3.09Hz), 5.90(1H, d, J=2.00 Hz).

MS:m/z225($M^+$).

Elementary analysis for $C_{22}H_{31}O_3F$: Calculated: C 72.89; H 8.62 Found: C 72.95; H 8.75

(4) 9α-Fluoro-17α-hydroxy-6α-methyl-4-pregnene-3,20-dione (11)

6-Methylpregnene (9) (40 mg), ethylene glycol (0.014 ml), and p-toluenesulfonic acid (2 mg) were added to benzene (20 ml), and refluxed with heat for 3 hours using a reflux condenser equipped with a moisture separator. The solvent was distilled off, and the residue was combined with an aqueous 5% $KHSO_4$ solution (5 ml) and acetone (5 ml). The mixture was refluxed for 2 hours at 70° C. The reaction mixture was concentrated and extracted with chloroform. The chloroform layer was washed with saturated brine, dried over $Na_2SO_4$, and concentrated. The residue was subjected to column chromatography (silica gel, 20 g) using 30% ethyl acetate/hexane as eluant, thereby obtaining an α-methylated derivative (11) (23 mg, 57.5% from compound (9)). Recrystallization from ethyl acetate afforded white crystals having a melting point of 237°–239° C.

[α] +23.76° (MeOH).

$^1$H-NMR ($CDCl_3$): δ 0.86(3H, s), 1.10(3H, d, J=6.45Hz), 1.30(3H, s), 2.69–2.79(2H, m), 2.99–3.03(1H, d, 3.84(1H, d, J=1.80Hz), 5.89(1H, d, J=1.80Hz).

MS:m/z362($M^+$).

Elementary analysis for $C_{22}H_{31}O_3F$: Calculated: C 72.89; H 8.62 Found: C 72.90; H 8.78

(5) 17α-Acetoxy-9α-fluoro-6α-methylprogesterone (1a)

9α-Fluoromedroxyprogesterone (11) (20 mg) was stirred for 5 hours at −10° C. in the presence of p-toluenesulfonic acid, acetic anhydride (0.4 ml), and methylene chloride (1 ml) under nitrogen. Water (10 ml) was added to the reaction mixture, and extraction was performed using chloroform. The chloroform layer was washed with an aqueous 5% NaHCO$_3$ solution and saturated brine, dried over Na$_2$SO$_4$, and concentrated. The residue was subjected to column chromatography (silica gel, 20 g) using 30% ethyl acetate/hexane as eluant, thereby obtaining 17α-acetoxy-9α-fluoro-6α-methylprogesterone (1a) (8 mg, 35.8%). Recrystallization from ethyl acetate/hexane afforded white crystals.

$[\alpha]_D^{20}$ +36.0° (c=0.210, CHCl$_3$).

$^1$H-NMR (500 MHz, CDCl$_3$) δ: 0.68(3H, s), 1.12(3H, d, J=6.5Hz), 1.31(3H, s), 2.05(3H, s), 2.10(3H, s), 2.96(1H, ddd, J=2.5, 11.3, 14.3Hz), 5.90(1H, d, J=1.5Hz).

$^{13}$C-NMR (126 MHz, CDCl$_3$) δ: 13.3, 17.9, 21.1, 21.3(d, J=5.4Hz), 23.6, 25.0(d, J=24Hz), 26.2, 26.8, 29.1(d, J=5.5Hz), 30.3, 33.1, 33.6, 34.4(d, J=3.0Hz), 37.6(d, J=21.0Hz), 43.3(d, J=21.8Hz), 44.6, 46.1, 96.2, 99.4(d, J=181Hz), 123.9, 169.8, 170.6, 198.7, 203.6.

MS:m/z 404(M$^+$).

High MS m/z (M$^+$) Calcd C$_{24}$H$_{33}$O$_4$F:404.2361, Found:404.2380.

IR (KBr) $v_{max}$ 1742, 1709, 1674 cm$^{-1}$.

m.p. 208°–210° C.

Example 2

(1) 17α-Acetoxy-11β,21-dihydroxy-6α-methyl-1,4-pregnadiene-3,20-dione (13)

To a solution (60 ml) of 6α-methylpredonisolone (6α-methyl-11β,17α,21-trihydroxy-1,4-pregnadiene-3,20-dione) (12) (2.13 g) in dichloromethane were added pyridinium p-toluenesulfonate (28.0 mg) and trimethyl orthoacetate (1.01 ml). The mixture was stirred at room temperature (20°–25° C.) for 5 hours. When the reaction was completed, the reaction mixture was concentrated, and the residue was dissolved in acetone. (30 ml). While cooling the mixture on ice, an aqueous solution (30 ml) of p-toluenesulfonic acid.H$_2$O (1.19 g) was added thereto. The mixture was stirred for 30 minutes on ice. Upon completion of reaction, a saturated aqueous NaHCO$_3$ solution was added and extraction was performed using ethyl acetate. After steps of washing with brine, drying over Na$_2$SO$_4$, evaporation of the solvent, and silica gel column chromatography (silica gel, 40 g) using 50% ethyl acetate/hexane as eluant, 17α-acetoxy-11β,21-dihydroxy-6α-methyl-1,4-pregnadiene-3,20-dione (13) (2.11 g, 89%) was obtained.

$[\alpha]_D^{20}$ +18.1° (c=0.490, CHCl$_3$).

$^1$H-NMR (500 MHz, CDCl$_3$) δ: 0.97(3H, s), 1.13(3H, d, J=6.0Hz), 1.46(3H, s), 2.02(3H, s), 2.74–2.82(1H, m), 4.24 (1H, dd, J=4.0, 18.0Hz), 4.33(1H, dd, J=3.5, 18.0 Hz), 6.04(1H, s), 6.28(1H, d, J=10.0 Hz), 7.25(1H, d, J=10.0Hz).

MS:m/z 416(M$^+$).

m.p. 159°–161° C.

(2) 17α-Acetoxy-11β-hydroxy-6α-methyl-1,4-prednadiene-3,20-dione (14)

To a solution (10 ml) of 17α-acetoxy-11β,21-dihydroxy-6α-methyl-1,4-pregnadiene-3,20-dione (13) (557 mg) in pyridine was added methanesulfonyl chloride (0.15 ml). The mixture was stirred at between 0° C. and 5° C. (exterior temperature) for 3 hours. After completion of reaction, iced water and ethyl acetate were added to the reaction mixture. The resultant mixture was sequentially washed with 10% HCl, a saturated aqueous NaHCO$_3$ solution, and brine, and then dried over Na$_2$SO$_4$. After the solvent was evaporated, the residue was dissolved in pyridine (10 ml). Sodium iodide (447 mg) was added to the solution, and the mixture was refluxed for 50 minutes. Upon completion of the reaction, a saturated aqueous Na$_2$SO$_3$ solution was added to the reaction mixture and extraction was performed using ethyl acetate. After steps of washing with 10% HCl, a saturated aqueous NaHCO$_3$ solution, and saturated brine and drying over Na$_2$SO$_4$, the solvent was evaporated, and the residue was subjected to silica gel column chromatography (silica gel=16 g) using 50% ethyl acetate/hexane as eluant, thereby obtaining 17α-acetoxy-11β-hydroxy-6α-methyl-1,4-pregnadiene-3,20-dione (14) (316 mg, 59%).

$[\alpha]_D^{20}$ +13.2° (c=0.430, CHCl$_3$).

$^1$H-NMR (500 MHz, CDCl$_3$) δ: 0.95(3H, s), 1.13(3H, d, J=6.5Hz), 1.46(3H, s), 2.06(3H, s), 2.05(3H, s), 2.90–2.98 (1H, m), 6.05(1H, t, J=2.0Hz), 6.29(1H, dd, J=2.0, 10.0Hz), 7.25(1H, d, J=10.0Hz).

MS:m/z 400(M$^+$).

m.p. 138°–140° C.

(3) 17α-Acetoxy-11β-hydroxy-6α-methyl-4-pregnene-3,20-dione (15)

To a solution (30 ml) of 17α-acetoxy-11β-hydroxy-6α-methyl-1,4-pregnadiene-3,20-dione (14) (316 mg) in dichloromethane-ethanol (1:1), chlorotris(triphenylphosphine)rhodium (I) (8.51 mg) was added. The mixture was stirred for 27 hours at room temperature (20°–25° C.) in a stream of hydrogen gas (1.5 kg/cm2). After completion of reaction, the reaction mixture was concentrated, and subjected to silica gel column chromatography (silica gel=10 g) using 50% ethyl acetate/hexane as eluant, thereby obtaining 17α-acetoxy-11β-hydroxy-6α-methyl-4-pregnene-3,20-dione (15) (285 mg, 90%).

$[\alpha]_D^{20}$ +55.4° (c=0.773, CHCl$_3$).

$^1$H-NMR (500 MHz, CDCl$_3$) δ: 0.93(3H, s), 1.06(3H, d, J=6.5Hz), 1.43(3H, s), 2.06(3H, s), 2.07(3H, s), 2.92–2.98 (1H, m), 5.73(1H, d, J=1.5Hz).

MS:m/z 362(M$^+$).

m.p. 193°–195° C.

(4) 17α-Acetoxy-9α-fluoro-6α-methylprogesterone (1a)

A solution of 17α-acetoxy-11β-hydroxy-6α-methyl-4-pregnene-3,20-dione (15) (145 mg) was dissolved in hydrogen fluoride pyridine (4.0 ml) at an exterior temperature of −15° C. The solution was stirred for 65 hours at the same exterior temperature of −15° C. When the reaction was completed, iced water was added to the reaction mixture, which was then extracted with ethyl acetate (50 ml, 30 ml). The organic layer was sequentially washed with 10% HCl, saturated NaHCO$_3$, and brine, and then dried over Na$_2$SO$_4$. After the solvent was evaporated, the residue was subjected to silica gel column chromatography (silica gel=6 g) using 40% ethyl acetate/hexane as eluant, thereby obtaining 17α-acetoxy-9α-fluoro-6α-methylprogesterone (1a) (37.9 mg, 26%).

Test Example 1

Neovascularization Inhibitory Activity

The neovascularization inhibitory activity was tested by a CAM (chorioallantoic membrane) method using the chorioallantoic membrane of a fertilized chicken egg. Briefly, two holes were made, using a drill, in the chorion of a fertilized chicken egg incubated in an incubator at 37° C. for 4.5 days. From a side hole, about 3 ml of egg white was removed by aspiration using an injector. The chorioallantoic membrane was separated from the chorion membrane in the lower section of the air cell, and subsequently, the chorion and chorion membrane in the upper section of the air cell were removed, to thereby expose the embryo and the chorioallantoic membrane. A chorioallantoic membrane having a diameter of 3–5 mm was used in the test. A silicone ring having an inner diameter of 3 mm was placed in the chorioallantoic membrane, cocentrically with the membrane. In the opening of the silicone ring, was placed one of EV (ethylene vinyl acetate copolymer) pellets containing various doses of the compound of the present invention. In a control group was placed an EV pellet containing no specimen. In a positive control group was placed medroxyprogesterone acetate (MPA), which is known to have neovascularization inhibitory activity.

The chicken egg was incubated for a further 2 days at 37° C., with the upper section of the chicken egg being covered with a metal cap coated with Teflon. In order to facilitate observation of the blood vessel network on the chorioallantoic membrane, a suitable amount of a fatty milk was injected to the inside of the chorioallantoic membrane.

The neovascularization inhibitory activity was assessed by measuring the avascular zone in the chorioallantoic membrane. The neovascularization inhibitory activity was assessed as positive when the avascular zone exceeded 3 mm in diameter. The frequency of thus-determined positive results was counted, and the results are shown in Table 1.

medium twice, and cultured in serum-free basal media (1 ml each) containing the compound of the present invention at a variety of concentrations. After incubation for 24 hours, the serum-free culture medium was recovered and subjected to centrifugation. The activity of uPA contained in the supernatant was measured using plasminogen and a synthetic substrate S-2251. The activity is indicated by the urokinase unit (U) per ml of culture supernatant. In view of the fact that medroxyprogesterone acetate, which exhibits neovascularization inhibitory action, suppresses uPA secretion from vascular endothelial cells, medroxyprogesterone acetate was used as a positive control. The results are shown in Table 2.

TABLE 2

| Compound | Concentration | uPA Activity (U/1 ml Culture supernatant)* |
|---|---|---|
| Compound (1a) | 0 | 0.88 ± 0.16 |
| | $10^{-9}$ | 0.71 ± 0.16 |
| | $10^{-8}$ | 0.61 ± 0.12 |
| | $10^{-7}$ | 0.36 ± 0.10 |
| | $10^{-6}$ | 0.22 ± 0.04 |
| MPA | $10^{-6}$ | 0.22 ± 0.05 |

*Mean ± S.D.

Example 3

Tablets each weighing 100 mg were prepared according to the following formulation.

TABLE 1

| Compound | Dose (µg/egg) | Number of chorioallantoic membranes used | Number of chorioallantoic membranes showing fields of no blood vessels | Frequency of emergence of fields of no blood vessels (%) | P value* |
|---|---|---|---|---|---|
| Compound (1a) | 0 | 26 | 0 | 0 | — |
| | 0.01 | 12 | 2 | 17 | >0.05 |
| | 0.1 | 12 | 4 | 33 | <0.05 |
| | 1 | 12 | 6 | 50 | <0.001 |
| | 10 | 12 | 9 | 75 | <0.001 |
| | 100 | 12 | 12 | 100 | <0.001 |
| MPA | 100 | 12 | 6 | 50 | <0.001 |
| | 300 | 12 | 9 | 75 | <0.001 |

*Statistical processing of the data regarding neovascularization inhibiting action was performed using a Fischer's accurate randomized test. P values satisfying P < 0.05 are considered to represent statistically significant results.

Test Example 2

Activity of urokinase-type Plasminogen Activator (uPA) Secreted by Vascular Endothelial Cells into a Culture Medium The effect exerted by the compound of the present invention on uPA secreted by vascular endothelial cells into a culture medium was measured by the following method. Briefly, vascular endothelial cells ($2\times10^5$ cells/well) were distributed into a 24-multiwell dish (product of Falcon), each well containing 1 ml of a basal culture medium (Dulbecco's modified Eagle's medium (DMEM)+25 mM HEPES+4.5 mg/ml glucose+0.584 mg/ml glutamine+100 units/ml penicillin+100 µg/ml streptomycin) supplemented with 10% fetal bovine serum. The dish was cultured in a humidified incubator (5% $CO_2$—95% air) at 37° C. for 16 hours. The cells were then washed using a serum-free basal

| Compound Example 1 | 10 (mg) |
|---|---|
| Lactose | 70 |
| Cornstarch | 16 |
| Hydroxypropylcellulose | 3 |
| Magnesium stearate | 1 |

Example 4

Tablets each weighing 100 mg were prepared according to the following formulation.

| Compound of Example 1 | 1 (mg) |
|---|---|
| Lactose | 75 |
| Cornstarch | 20 |

-continued

|  |  |
|---|---|
| Hydroxypropylcellulose | 3 |
| Magnesium stearate | 1 |

Example 5

Tablets each weighing 100 mg were prepared according to the following formulation.

|  |  |
|---|---|
| Compound Example 1 | 10 (mg) |
| β-Cyclodextrin | 30 |
| Lactose | 46 |
| Cornstarch | 10 |
| Hydroxypropylcellulose | 3 |
| Magnesium stearate | 1 |

Example 6

Tablets each weighing 100 mg were prepared according to the following formulation.

|  |  |
|---|---|
| Compound of Example 1 | 1 (mg) |
| β-Cyclodextrin | 3 |
| Lactose | 64 |
| Cornstarch | 28 |
| Hydroxypropylcellulose | 3 |
| Magnesium stearate | 1 |

As described above, it was confirmed that the compound of the present invention exhibits neovascularization inhibitory action and suppresses secretion by vascular endothelial cells of plasminogen activator. Moreover, it was found that the neovascularization inhibitory action of the compound of the present invention is not less than 20 times as potent as that of conventionally known neovascularization inhibitory substance, medroxyprogesterone acetate.

INDUSTRIAL APPLICABILITY

The compound (1) of the present invention possesses a potent neovascularization inhibitory effect, and thus is useful as a remedy for malignant tumors, diabetic retinitis, and rheumatism based on the neovascularization inhibition.

We claim:

1. A progesterone compound represented by the following formula (1):

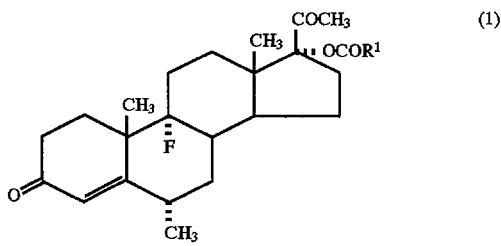

wherein $R^1$ represents a C1–C23 hydrocarbon group.

2. The progesterone compound according to claim 1, wherein $R^1$ is C1–C17 alkyl.

3. The progesterone compound according to claim 1, wherein $R^1$ is methyl or n-pentadecyl.

4. A method of inhibiting neovascularization comprising administering to patient in need thereof an effective amount of the progesterone compound as defined in claim 1 as an active ingredient.

5. A pharmaceutical composition comprising a progesterone compound as defined in claim 1, and a carrier for pharmaceuticals.

6. A method for the treatment of malignant tumors, diabetic retinitis, or rheumatism, characterized by administering an effective amount of the progesterone compound as defined in claim 1, to a patient in need thereof.

* * * * *